United States Patent [19]

O'Neil et al.

[11] Patent Number: 5,128,396
[45] Date of Patent: Jul. 7, 1992

[54] COATING COMPOSITIONS CONTAINING WATER-INSOLUBLE SALTS OF KETO-ACIDS

[75] Inventors: Robert M. O'Neil, Flixton; Emyr Phillips, Tingley; Robert C. Wasson, Penketh, all of England

[73] Assignee: Ciba-Geigy Corporation, Ardsley, N.Y.

[21] Appl. No.: 561,557

[22] Filed: Aug. 1, 1990

[30] Foreign Application Priority Data

Aug. 8, 1989 [GB] United Kingdom ............... 8918086

[51] Int. Cl.$^5$ ..................... C08K 5/10; C23F 11/00
[52] U.S. Cl. ......................... 524/288; 524/98; 524/99; 524/104; 524/289; 252/392; 106/14.16; 106/14.18
[58] Field of Search ................. 106/14.18, 14.16; 252/392; 524/288

[56] References Cited

U.S. PATENT DOCUMENTS 4,131,583 12/1978 Boerwinkle ............... 106/14.18
4,909,987 3/1990 Penninger et al. ........... 252/388

OTHER PUBLICATIONS

Derwent Abst. 82-52752e/26.
Derwent Abst. 82-50433e/25.

Primary Examiner—Paul R. Michl
Assistant Examiner—Tae H. Yoon
Attorney, Agent, or Firm—Luther A. R. Hall

[57] ABSTRACT

The present invention provides coating compositions comprising
 a) an organic film-forming binder; and
 b) a corrosion-inhibiting amount of a salt of
  i) a ketoacid having the formula (I):

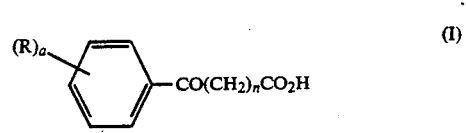

wherein a is 1,2,3,4 or 5; the R substituents are the same or different and each is hydrogen; halogen; nitro; cyano; $CF_3$; $C_1$-$C_{15}$ alkyl; $C_5$-$C_{12}$ cycloalkyl; $C_2$-$C_{15}$ alkenyl; $C_1$-$C_{12}$ halogenoalkyl; $C_1$-$C_{12}$ alkoxy; $C_1$-$C_{12}$ thioalkyl; $C_6$-$C_{12}$ aryl; $C_6$-$C_{10}$ aryloxy; $C_7$-$C_{12}$ alkaryl; —$CO_2R_1$ in which $R_1$ is a) hydrogen, b) $C_1$-$C_{20}$ alkyl optionally interrupted by one or more O—, N— or S—atoms, c) $C_7$-$C_{12}$ alkaryl or d) $C_6$-$C_{12}$ aryl optionally substituted with one or more carboxy groups; —$COR_1$ in which $R_1$ has its previous significance; $NR_2R_3$ in which $R_2$ and $R_3$ are the same or different and each is hydrogen or $C_1$-$C_{24}$ alkyl optionally interrupted by one or more O,S or NH moieties; or when a is 2, 3, 4 or 5, two adjacent groups R may be the atoms required to form a fused benzene or cyclohexyl ring; and n is an integer from 1 to 10; and
  ii) an amine of formula II:

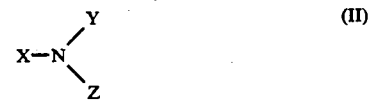

wherein X, Y and Z are the same or different, and are hydrogen; $C_4$-$C_{24}$ alkyl optionally interrupted by one or more O-atoms; phenyl; $C_7$-$C_9$ phenylalkyl; $C_7$-$C_9$ alkylphenyl; or two of X, Y and Z together with the N-atom to which they are attached from a 5—, 6— or 7-membered heterocyclic residue, which optionally contains a further oxygen, nitrogen or sulphur atom and which is optionally substituted by one or more $C_1$-$C_4$ alkyl, amino, hydroxy, carboxy or $C_1$-$C_4$ carboxy alkyl groups, and the other of X, Y and Z is hydrogen; provided that X, Y and Z are not simultaneously hydrogen.

The salts derived from ketoacids of Formula I and amines of Formula II are new compounds.

16 Claims, No Drawings

COATING COMPOSITIONS CONTAINING WATER-INSOLUBLE SALTS OF KETO-ACIDS

The present invention relates to coating compositions, in particular those containing, as corrosion inhibitors, certain amine salts of ketoacids, as well as to these salts which are novel.

Protection against corrosion is one of the most important functions of organic coating compositions for metal substrates. Many suggestions for improving the protection of coatings against corrosion are to be found in the literature, for example in H. Kittel, Lehrbuch der Lacke und Beschichtungen ("Textbook of Paints and Coatings"), volume V, Stuttgart 1977, 46-103.

On the one hand, the barrier function of the coating composition can be improved, in order to keep corrosive agents, such as oxygen, water and ions, away from the metal surface. On the other hand, it is possible to employ corrosion-inhibiting pigments which intervene chemically or electrochemically in the corrosion process, for example by the formation of insoluble deposits with corrosion products or by passivation (polarisation) of the metal surface. Metal chromates and lead compounds rank amongst the most effective corrosion-inhibiting pigments. Much use has been made of metal chromates, particularly because they inhibit both anodic and cathodic corrosion. Nowadays there are certain objections to the use of chromates owing to their potential carcinogenic action. Similarly, there are objections to the use of lead compounds owing to their chronic toxicity.

We have now found that certain amine salts of ketoacids impart excellent corrosion inhibiting properties when incorporated into coating compositions.

Accordingly, the present invention provides coating compositions comprising
a) an organic film-forming binder; and
b) a corrosion-inhibiting amount of a water-insoluble salt of
i) a ketoacid having the formula (I):

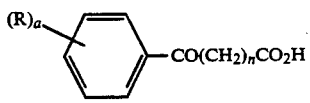

wherein a is 1, 2, 3, 4 or 5; the R substituents are the same or different and each is hydrogen; halogen; nitro; cyano; $CF_3$; $C_1$-$C_{15}$ alkyl; $C_5$-$C_{12}$ cycloalkyl; $C_2$-$C_{15}$ alkenyl; $C_1$-$C_{12}$ halogenoalkyl; $C_1$-$C_{12}$ alkoxy; $C_1$-$C_{12}$ thioalkyl; $C_6$-$C_{12}$ aryl; $C_6$-$C_{10}$ aryloxy; $C_7$-$C_{12}$ alkaryl; $-CO_2R_1$ in which $R_1$ is a) hydrogen, b) $C_1$-$C_{20}$ alkyl optionally interrupted by one or more O—, N— or S—atoms, c) $C_7$-$C_{12}$ alkaryl or d) $C_6$-$C_{12}$ aryl optionally substituted with one or more carboxy groups; $-COR_1$ in which $R_1$ has its previous significance; $NR_2R_3$ in which $R_2$ and $R_3$ are the same or different and each is hydrogen or $C_1$-$C_{24}$ alkyl optionally interrupted by one or more O, S or NH moieties; or when a is 2, 3, 4 or 5, two adjacent groups R may be the atoms required to form a fused benzene or cyclohexyl ring; and n is an integer from 1 to 10; and
ii) an amine of formula II:

wherein X, Y and Z are the same or different, and are hydrogen; $C_4$-$C_{24}$ alkyl optionally interrupted by one or more O-atoms; phenyl; $C_7$-$C_9$ phenylalkyl; $C_7$-$C_9$ alkylphenyl; or two of X, Y and Z together with the N-atom to which they are attached form a 5-, 6- or 7-membered heterocyclic residue, which optionally contains a further oxygen, nitrogen or sulphur atom and which is optionally substituted by one or more $C_1$-$C_4$ alkyl, amino, hydroxy, carboxy or $C_1$-$C_4$ carboxy alkyl groups, and the other of X, Y and Z is hydrogen; provided that X, Y and Z are not simultaneously hydrogen.

When a is 3, 4 or 5 and R is alkyl, alkenyl, halogenoalkyl, alkoxy or thioalkyl, then such substituents R preferably contain up to 4 carbon atoms. If the phenyl group is substituted by $CF_3$, cycloalkyl, aryl, aryloxy, alkaryl, $-CO_2R_1$, $-COR_1$ or $NR_2R_3$ as R groups, preferably only 1 or 2, in particular one of these substituents is present. Preferred R substituents are, independently, hydrogen, $C_1$-$C_{15}$ alkyl, $C_5$-$C_6$ cycloalkyl, $C_2$-$C_{15}$ alkenyl, $C_1$-$C_6$ halogenoalkyl, halogen, $C_1$-$C_6$ alkoxy, phenyl, benzyl, $-COOH$, $-COO-C_1$-$C_4$ alkyl, $-CO-C_1$-$C_4$ alkyl or $NR_2R_3$ with $R_2$ and $R_3$ being hydrogen or $C_1$-$C_{12}$ alkyl or two R's together form a fused benzo ring.

Particularly preferred R substituents are hydrogen, $C_1$-$C_{15}$ alkyl, halogen, $C_1$-$C_6$ alkoxy, or two R's together form a fused benzo ring. Preferably, if not all R's are hydrogen, one R substituent which is not hydrogen, is located in the para position.

Examples of halogen atoms R are fluorine, chlorine, bromine and iodine, especially fluorine, chlorine or bromine, in particular chlorine and bromine. $C_1$-$C_{15}$ alkyl groups R include methyl, ethyl, n-propyl, isopropyl, n-butyl, sec.-butyl, tert.-butyl, n-pentyl, n-hexyl, n-octyl, n-decyl, n-dodecyl, n-tetradecyl and n-pentadecyl. $C_5$-$C_{12}$ cycloalkyl groups R include cyclopentyl, cyclohexyl, cyclooctyl, cyclodecyl and cyclododecyl. $C_2$-$C_{15}$ alkenyl groups R are preferably $C_2$-$C_7$ alkenyl groups and may be e.g. vinyl, 2-propenyl (allyl), but-1-en-3-yl, but-3en-1-yl, (2-methyl)-prop-2-en-1-yl (isobutenyl), pent-1-enyl, (5-methyl) but-2-en-1-yl, hex-1-enyl or hept-1-enyl; $C_1$-$C_{12}$ halogenoalkyl groups R include, e.g. chloromethyl, bromoethyl, fluoropropyl, isobutyl, chloropentyl, chlorohexyl, chlorooctyl, chlorodecyl and chlorododecyl. $C_1$-$C_{12}$ alkoxy groups R include methoxy, ethoxy, propoxy, butoxy, hexyloxy, octyloxy, decyloxy and dodecyloxy. $C_1$-$C_{12}$ thioalkyl groups R include thiomethyl, thioethyl, thiopropyl, thiobutyl, thiopentyl, thiohexyl, thiooctyl, thiodecyl and thiododecyl. $C_6$-$C_{10}$ aryl groups R are e.g. phenyl or naphthyl groups. $C_7$-$C_{12}$ aralkyl groups R include benzyl, naphth-2-ylmethyl, 1- or 2-phenylethyl or 2- or 3-phenylpropyl. $C_6$-$C_{10}$ aryloxy is e.g. phenoxy or naphthoxy. $CO_2R_1$ groups R include, e.g. carboxy, carboxymethyl, carboxyethyl, carboxydecyl, carboxyeicosyl, carboxymethoxymethyl, carboxymethylthiomethyl or carboxymethylaminomethyl; carboxymethylphenyl or carboxymethylnaphthyl; and carboxyphenyl or carboxynaphthyl. $COR_1$ groups R are, e.g. the acetaldehyde group, acetyl, propionyl, butyroyl, dodecanoyl, eicosanyl, carbonylmethoxymethyl, benzoyl or naphthoyl. $NR_2R_3$ groups R are, e.g. methylamino, ethylamino, propylamino, n-butylamino, hexylamino, octylamino, dodecylamino, octadecylamino, eicosylamino, tetracosylamino, dimethylamino, diethylamino, di-n-butylamino, di-n-octylamino, di-n-dodecylamino, di-n-octadecylamino, di-n-eicosylamino, di-n-tetracosylamino, methoxymethylamino, methylthiomethylamino and methylaminomethylamino.

Preferably, R is H or $C_1$–$C_{15}$ alkyl and a is 1, 2, 3 or 4. $C_4$–$C_{24}$ alkyl groups X, Y and Z, preferably contain 6–24, especially 8–14 C-atoms. Examples are n-butyl, sec.-butyl, tert.-butyl, n-pentyl, n-hexyl, n-octyl, n-nonyl, n-decyl, n-dodecyl, n-tetradecyl, n-hexadecyl, n-octadecyl, n-eicosyl and n-tetraeicosyl.

$C_4$–$C_{24}$ alkyl radicals X, Y and Z interrupted by one or more oxygen atoms include, e.g. 2-ethoxypropyl, 1-methoxybutyl, n-butoxymethyl, 1-methoxyoctyl, 1-methoxydecyl, 1-methoxydodecyl, 1-methoxyhexadecyl, 1-methoxyeicosyl, 1-methoxytetraeicosyl and 2-methoxyethoxymethyl.

$C_7$–$C_9$ phenylalkyl groups X, Y and Z are e.g. benzyl, 1-phenylethyl, 2-phenylethyl, α-methylbenzyl, α, α-dimethylbenzyl or 3-phenylpropyl. $C_7$–$C_9$ alkylphenyl groups X, Y and Z include e.g. tolyl, xylyl, ethylphenyl and propylphenyl.

Heterocyclic groups formed by two of X, Y and Z are preferably saturated ones, in particular 6-membered, examples of which are piperidino, morpholino, thiomorpholino, piperazino and 4-$C_1$–$C_4$ alkyl-piperazino.

Specific examples of ketoacids of formula I include e.g. benzoylacetic acid, 4-chlorobenzoylacetic acid, 4-bromobenzoylacetic acid, 4-nitrobenzoylacetic acid, 4-trifluoromethylbenzoylacetic acid, 4-methylbenzoylacetic acid, 2,4-dimethylbenzoylacetic acid, 4-cyclopentylbenzoylacetic acid, 4-cyclohexylbenzoylacetic acid, 2-propenylbenzoylacetic acid, 4-chloromethylbenzoylacetic acid, 4-methoxybenzoylacetic acid, 4-thiomethylbenzoylacetic acid, 4-phenylbenzoylacetic acid, 4-naphthylbenzoylacetic acid, 4-phenoxybenzoylacetic acid, 4-naphthoxybenzoylacetic acid, 4-tolylbenzoylacetic acid, 4-methylnaphthylbenzoylacetic acid, 4-carboxybenzoylacetic acid, 4-methylcarboxybenzoylacetic acid, benzoylpropionic acid, 4-chlorobenzoylpropionic acid, 4-methylbenzoylpropionic acid, 4-nitrobenzoylpropionic acid, 2,6-dimethylbenzoylpropionic acid, 2-propenylbenzoylpropionic acid, 4-chloromethylbenzoylpropionic acid, 4-methoxybenzoylpropionic acid, 2-thiomethylbenzoylpropionic acid, benzoylbutyric acid, 4-cyanobenzoylbutyric acid, 4-methylbenzoylbutyric acid, 4-chlorobenzoylbutyric acid, benzoylpentanoic acid, 4-nitrobenzoylpentanoic acid, 4-methylbenzoylpentanoic acid, 4-chlorobenzoylpentanoic acid, benzoylhexanoic acid, 4-methylbenzoylhexanoic acid, 4-chlorobenzoylhexanoic acid, benzoylheptanoic acid, 4-methylbenzoylheptanoic acid, benzoyloctanoic acid, 4-methylbenzoyloctanoic acid, benzoylnonanoic acid, 4-methylbenzoylnonanoic acid, benzoyldecanoic acid, 4-methylbenzoyldecanoic acid, benzoylundecanoic acid, 4-methylbenzoylundecanoic acid.

Specific examples of amines of formula II include: n-butylamine, iso-butylamine, tert.-butylamine, n-/iso-/tert.-amylamine, n-hexylamine, n-heptylamine, n-octylamine, iso-octylamine, tert.-octylamine, n-nonylamine, n-decylamine, n-dodecylamine, iso-dodecylamine, tert.-dodecylamine, n-tridecylamine, iso-tridecylamine, tert.-dodecylamine, n-tridecylamine, iso-tridecylamine, tert.-tridecylamine, n-tetradecylamine, iso-tetradecylamine, tert.-tetradecylamine, n-octadecylamine, iso-octadecylamine, tert.-octadecylamine, n-nonadecylamine, iso-nonadecylamine, tert.-nonadecylamine, n-eicosamine, iso-eicosamine, tert.-eicosamine, n-heneicosamine, isoheneicosamine, tert.-heneicosamine, n-docosamine, iso-docosamine, tert.-docosamine, n-tricosamine, iso-tricosamine, tert.-tricosamine, n-tetracosamine, iso-tetracosamine, tert.-tetracosamine, benzylamine, di-benzylamine, N-benzylaniline, di-n-butylamine, di-isobutylamine, di-isodecylamine, di-tridecylamine, di-isooctylamine, di-tert.octylamine, di-isotetradecylamine, di-n-octadecylamine, di-t-butylamine, di-n-octylamine, di-2-ethylhexylamine, di-n-dodecylamine, di-n-eicosylamine, di-n-tetraeicosylamine, 3-butoxypropylamine, hexoxybutylamine, nonyloxypropylamine, aniline, N-methylaniline, N-ethylaniline, tri-n-butylamine, tri-isobutylamine, tri-n-octylamine or mixtures thereof.

In formula I n is preferably 1 to 8, in particular 1 to 4, for example 2 or 3. As to the substituents X, Y and Z in formula II, in preferred compounds at least one of them, in particular 2 of them, is (are) hydrogen (secondary or primary amines). Those X, Y and Z which are not hydrogen, are preferably $C_4$–$C_{24}$ alkyl, phenyl or benzyl, especially $C_6$–$C_{24}$ alkyl, in particular $C_8$–$C_{14}$ alkyl.

Also preferred are compositions of this invention wherein in formulae I and II a is 1 to 4, R is hydrogen, $C_1$–$C_{15}$ alkyl, halogen, $C_1$–$C_4$ alkoxy or, if a is at least 2, two adjacent groups R form a fused benzo ring, n is 2 to 7, X is $C_8$–$C_{14}$ alkyl and Y and Z are hydrogen.

The ketoacids of formula I and the amines of formula II are not new, in fact many are readily available commercially. The ketoacids of formula I in which n is 2 or 3 have been described, along with related compounds, in German Offenlegungsschrift 3338953. This German patent specification describes the said ketoacids or their water-soluble alkali-, ammonium-, ammonia or alkanolamine salts, as useful corrosion inhibitors in aqueous systems e.g. detergents, coolants, hydraulic fluids or cooling waters. No mention is made of the use of the said ketoacids, or the specified salts, as corrosion inhibitors in specific aqueous systems such as paints. No mention is also made to water-insoluble amine salts of said ketoacids.

The water-insoluble salt component b) of coating compositions of the invention may be prepared from the ketoacids of formula I and the amines of formula II by heating these reactants together at 30°–130° C., preferably at 50°–60° C., optionally in a solvent e.g. methanol, xylene, or tetrahydrofuran.

The water-insoluble salts derived from a ketoacid of formula I and an amine of formula II are new and are a further object of this invention. Preferred compounds and substituents are the same as described above in the compositions of this invention.

The organic film-forming binder component a) of the coating compositions of the present invention may be any film-former suitable for solvent-based, but in particular for aqueous-based coating compositions. Examples of such film-forming binders are epoxide resins, polyurethane resins, aminoplast resins or mixtures of such resins; or a basic aqueous dispersion, or solution of an acidic resin.

Of particular interest are organic film-forming binders for aqueous-based coating compositions e.g. alkyd resins; acrylic resins; two-pack epoxy resins; polyester resins which are usually saturated; water-dilutable phenolic resins or dispersions thereof; water-dilutable urea resins; and vinyl/acrylic copolymer resins.

More specifically, the alkyd resins may be water-dilutable alkyds such as air-drying or bake systems which may also be used in combination with water-dilutable melamine resins; or alkyd emulsions either oxidatively- or air-drying or bake systems, optionally used in combination with water-borne acrylics or copolymers thereof, vinyl acetates etc.

Acrylic resins may be straight acrylics; acrylic acid ester copolymers; combinations or copolymers with vinyl resins e.g. vinyl acetate, or with styrene. These systems may be air-drying or bake systems.

Water-dilutable epoxide resins, in combination with suitable polyamine curing agents have good mechanical and chemical stability. By the polyaddition of epoxide resin with amine, thermosets are obtained having very high film hardness. The addition of organic solvents is not necessary when liquid epoxy-based resins are used for aqueous systems.

When using epoxide-solid resin dispersions, a minor amount of solvent is necessary for improved film formation.

Preferred epoxide resins are those based on aromatic polyols, in particular bisphenols. The epoxide resins are used in conjunction with a curing agent. The latter can be, in particular, an amino or hydroxy compound or an acid or an acid anhydride or a Lewis acid. Examples of these are polyamines, polyaminoamides, polysulfide polymers, polyphenols, boron fluoride and complexes thereof, polycarboxylic acids, 1,2-dicarboxylic acid anhydrides or pyromellitic dianhydride.

In addition to the components a) and b), the coating compositions of the invention can also contain further components, for example pigments, dyes, extenders and other additives such as are customary for coating compositions. The pigments can be organic, inorganic or metallic pigments, for example titanium dioxide, iron oxide, aluminium bronze, phthalocyanine blue etc. It is also possible to use concomitantly anti-corrosion pigments, for example pigments containing phosphates or borates, metal pigments and metal oxide pigments (see Farbe und Lack 88 (1982), 183) or the pigments described in European Patent A 54,267. Examples of extenders which can be used concomitantly are talc, chalk, alumina, baryte, mica or silica. Examples or further additives are flow control auxiliaries, dispersing agents, thixotropic agents, adhesion promoters, antioxidants, light stabilisers or curing catalysts.

Particular importance attaches to the addition of basic extenders or pigments. In certain binder systems, for example in acrylic and alkyd resins, these produce a synergistic effect on the inhibition of corrosion. Examples or such basic extenders or pigments are calcium carbonate, magnesium carbonate, zinc oxide, zinc carbonate, zinc phosphate, magnesium oxide, aluminium oxide, aluminium phosphate or mixtures thereof. Examples of pigments are those based on aminoanthraquinone.

Finally, the corrosion inhibitor can also be applied to a neutral carrier. Suitable carriers are, in particular, pulverulent extenders or pigments. This technique is described in greater detail in German Offenlegungsschrift 3,122,907.

In addition to the component b), the coating composition can also contain another organic, metal-organic or inorganic corrosion inhibitors, for example salts of nitroisophthalic acid, tannin, phosphoric esters, technical amines, substituted benztriazoles or substituted phenols, such as are described in German Offenlegungsschrift 3,146,265.

The coating compositions according to the invention are preferably used as a primer on metallic substrates, in particular on iron, steel, copper, aluminium, aluminium alloys or zinc. Here they can function as so-called conversion coatings, in that chemical reactions take place at the interface between the metal and the coating. The application of the coatings can be effected by the customary methods, such as spraying, brushing, rollercoating, dipping or electrodeposition, in particular cathodic deposition. Depending on whether the filmformer is a resin which dries physically or can be cured by heat or radiation, the curing of the coatings is carried out at room temperature, by stoving or by irradiation.

The corrosion inhibitors can be added to the coating composition during the preparation of the latter, for example during the distribution of the pigment by grinding. The inhibitor is used in an amount of 0.01–20% by weight, preferably 0.5–5% by weight, based on the solids content of the coating composition.

Recently, there has been an increased commercial interest in the production of surface coatings by electrodeposition viz. the deposition of a film-forming material under the influence of an applied electrical potential. Various coating materials have been developed for this method of application, but the technique is often associated with various disadvantages. In particular, it is difficult to attain desired levels of corrosion inhibition using this method of applying surface coatings.

We have now found that the water-insoluble salt component b) of the coating compositions of the present invention imparts excellent corrosive-inhibiting properties to both cathodic and anodic electrocoats.

As component a) of the electrodepositable cathodic aqueous coating compositions of the present invention, there may be used e.g. an epoxy resin optionally crosslinked with a capped or blocked organic polyisocyanate; acrylic resins optionally and preferably crosslinked with a capped or blocked isocyanate; acrylic or other unsaturated resins crosslinked via double bonds; adducts of epoxy resins with amines, polycarboxylic acids or their anhydrides or aminocarboxylic, mercaptocarboxylic or aminosulphonic acids; polyurethanes; polyesters; and reaction products of phenolic hydroxyl group-containing resins with an aldehyde and an amine or amino- or mercapto-carboxylic or aminosulphonic acid; as well as mixtures of these resins.

Preferred adducts of an epoxide resin with an amine are adducts of a polyglycidyl ether, which may be of a polyhydric phenol or a polyhydric alcohol, with a monoamine. Suitable polyglycidyl ethers include those of dihydric alcohols such as butane-1,4-diol, neopentyl glycol, hexamethylene glycol, oxyalkylene glycols and polyoxyalkylene glycols, and trihydric alcohols such as glycerol, 1,1,1-trimethylolpropane and adducts of these alcohols with ethylene oxide or propylene oxide. It will be understood by those skilled in the art that these polyglycidyl ethers of polyhydric alcohols are usually advanced, i.e. converted into longer chain higher molecular weight polyglycidyl ethers, for example by reaction with a dihydric alcohol or phenol, so that the resulting polyglycidyl ethers given adducts with suitable electrodepositable film-forming properties on reaction with the secondary monoamine. Preferred polyglycidyl ethers are those of polyhydric phenols, including bisphenols such as bisphenol F, bisphenol A and tetrabromobisphenol A and phenolic novolak resins such as phenol-formaldehyde or cresol-formaldehyde novolak resins. These polyglycidyl ethers of phenols may have been advanced, for example by reaction with dihydric alcohols or phenols such as those hereinbefore described. Particularly preferred polyglycidyl ethers are polyglycidyl ethers of bisphenol A advanced by reaction with bisphenol A.

Monoamines suitable for adduct formation with the polyglycidyl ethers include primary, secondary or tertiary amines. Secondary amines are preferred e.g. dialkylamines such as diethylamine, di-n-propylamine, di-isopropylamine, di-n-butylamine, di-n-octylamine and di-n-dodecylamine or nitrogen heterocycles such as piperidine or morpholine.

Preferred secondary monoamines are secondary alkanolamines such as diethanolamine, N-methylethanolamine, N-butylethanolamine, diisopropanolamine, N-methylisopropanolamine or di-n-butanolamine. A particularly preferred secondary alkanolamine is diethanolamine.

Thus preferred adducts of polyglycidyl ether with a secondary monoamine are adducts of a polyglycidyl ether of a polyhydric phenol, which may have been advanced, with a secondary alkanolamine, while particularly preferred such adducts are those of a polyglycidyl ether of bisphenol A, advanced by reaction with bisphenol A, with diethanolamine.

Electrodeposition of the organic resin may be carried out using conventional procedures. The pigments can be organic, inorganic or metallic pigments, for example titanium dioxide, iron oxide, aluminium bronze, phthalocyanine blue etc. It is also possible to use concomitantly anti-corrosion pigments, for example pigments containing phosphates or borates, metal pigments and metal oxide pigments (see Farbe und Lack 88 (1982), 183) or the pigments described in European Patent 54,267.

The corrosion inhibitor component b) may be added to the electrodepositable coating system during the preparation of the latter, for example, during the distribution of the pigment by grinding e.g. by the methods disclosed in EP 107089. Alternatively, the corrosion inhibitors can be incorporated into the non-emulsified resins and also into the grind resin. The corrosion inhibitors are preferably used in an amount of 0.01 to 20% by weight, preferably 0.05 to 5% by weight, based on the solids content of the electro-depositable coating composition.

Electrodeposition for only a few minutes, usually one minute, at a voltage of up to 500 volts is sufficient in most cases. Usually, voltage programs, viz. stepwise increase of the voltage, are used.

The coating compositions of the present invention may be applied to any electrically conductive substrate especially metals such as iron; steel; e.g. cold-rolled steel, optionally treated with zinc phosphate or galvanized; copper; zinc; and aluminium; more especially zinc or aluminium alloys.

After electrodeposition of the organic resin film, the substrate is rinsed with de-mineralized water, air-blasted and baked at elevated temperature e.g. up to 500° F.

Further objects of this invention are the use of a coating composition as a primer coating on metal substrates, in particular on iron, steel, copper, aluminium, aluminium alloys or zinc, as well as a method of producing an organic, corrosion-resistant surface coating on a corrodable metal surface comprising treating the corrodable metal surface with a composition according to this invention, then dry or curing the coating composition to produce a dried or cured surface coating on the metal surface.

The following Examples further illustrate the present invention. Examples 1 to 6 illustrate the preparation of the water-insoluble corrosion inhibitor salts used in the compositions of the present invention. Percentages are by weight, if not otherwise stated.

EXAMPLE 1

9.0 parts of 3-(4-methylbenzoyl)propionic acid dissolved in 50 parts tetrahydrofuran are treated with 9.3 parts of tert.-tridecylamine. The resulting solution is heated at 60° C. for 30 minutes, cooled and evaporated to give 17.1 parts tert.-tridecylammonium 3-(4-methylbenzoyl)propionate as a yellow oil.

Elemental analysis: Calculated: C, 73.7; H, 10.5; N, 3.6%. Founded: C, 73.4; H, 10.9; N, 3.9%.

EXAMPLE 2

10.3 parts of 3-(2,4-dimethylbenzoyl)propionic acid dissolved in 50 parts tetrahydrofuran are treated with 10 parts of tert.-tridecylamine. Using the procedure in Example 1 gives 20 parts tert.-tridecylammonium 3-(2,4-dimethylbenzoyl)propionate as a yellow oil.

Elemental analysis: Calculated: C, 74.1; H, 10.6; N, 3.5%. Found: C, 74.1; H, 11.1; N, 3.9%.

EXAMPLE 3

Treatment of 3-(2,4,6-trimethylbenzoyl)propionic acid with tert.-tridecylamine in the manner described in Example 1 gives tert.-tridecylammonium 3-(2,4,6-trimethylbenzoyl)propionate.

Elemental analysis: Calculated: C, 74.5; H, 10.7; N, 3.3%. Found: C, 74.3; H, 11.2; N, 3.7%.

EXAMPLE 4

Treatment of 3-(2,3,5,6-tetramethylbenzoyl)propionic acid with tert.-tridecylamine in the manner described in Example 1 gives tert.-tridecylammonium 3-(2,3,5,6-tetramethylbenzoyl)propionate.

Elemental analysis: Calculated: C, 74.8; H, 10.9; N, 3.2%. Found: C, 74.5; H, 10.7; N, 3.5%.

EXAMPLE 5

Treatment of 3-(4-dodecylbenzoyl)propionic acid with tert.-tridecylamine in the manner described in Example 1 gives tert.-tridecylammonium 3-(4-dodecylbenzoyl)-propionate.

Elemental analysis: Calculated: C, 77.0; H, 11.6; N, 2.6%. Found: C, 76.7; H, 11.4; N, 2.5%.

EXAMPLE 6

Treatment of 3-(2-naphthoyl)propionic acid with tert.-tridecylamine in the manner described in Example 1 gives tert.-tridecylammonium 3-(2-naphthoyl)propionate.

Elemental analysis: Calculated: C, 75.9; H, 9.6; N, 3.3%. Found: C, 75.5; H, 9.9; N, 3.6%.

EXAMPLES 7 to 12

An aqueous alkaline paint formulation having a solids content of 56.15 wt % is prepared using the following formulation:

60.03 wt % Bayhydrol B (30% in water)

0.14 wt % Servosyn WEB (8%)
0.28 wt % Ascinin
18.18 wt % Bayferrox 130M
5.15 wt % Heladol 10
10.6 wt % Micronised talc
0.2 wt % Aerosil 300
1.06 wt % ZNO
0.9 wt % butylglycol
0.05 wt % aluminium octoate
0.46 wt % water
1.12 wt % (2% by weight on solids content) of each of Examples 1 to 6 is dispersed in separate samples of the paint formulation.

Each paint sample is applied on to cold roll steel plates at a layer thickness of 55–60 microns, and dried for 72 hours at 20° C. A scribe (70×0.5 mm) is applied as a defined damage of the coating.

The painted plates are then placed in a sealed chamber and exposed for 840 hours to condensed moisture at 40° C./100% relative humidity.

The results are summarized in the following Table I:

TABLE I

| Example | Corrosion inhibiting additive | % Additive | Assessment of coating | Assessment of metal | C.P. |
| --- | --- | --- | --- | --- | --- |
| — | Control | Nil | 3.4 | 1.5 | 4.9 |
| 7 | Product of Ex. 1 | 2 | 6.0 | 5.8 | 11.8 |
| 8 | Product of Ex. 2 | 2 | 6.0 | 5.8 | 11.8 |
| 9 | Product of Ex. 3 | 2 | 5.9 | 3.8 | 9.7 |
| 10 | Product of Ex. 4 | 2 | 5.2 | 5.7 | 10.9 |
| 11 | Product of Ex. 5 | 2 | 4.2 | 1.8 | 6.0 |
| 12 | Product of Ex. 6 | 2 | 5.9 | 5.8 | 11.7 |

A similar series of painted plates is also scribed and subjected to a salt spray test procedure (168 hours) as specified in ASTM B117.

At the end of the test, the coating is removed and the corrosion of the metal at the cross-cut (as specified in DIN 53,167) and the remainder of the surface is assessed. In every case, the assessment is made on the basis of a 6-stage scale. The corrosion protection value (CP) is given by the sum of the assessment of the coating and the metal surface. The higher this value, the more effective the inhibitor under test.

The results of the salt spray test are summarized in Table II:

TABLE II

| Example | Corrosion inhibiting additive | % Additive | Assessment of coating | Assessment of metal | C.P. |
| --- | --- | --- | --- | --- | --- |
| 13 | Control | Nil | 3.0 | 0.6 | 3.6 |
| 14 | Product of Ex. 1 | 2 | 5.2 | 5.6 | 10.8 |
| 15 | Product of Ex. 2 | 2 | 4.9 | 5.5 | 10.4 |
| 16 | Product of Ex. 3 | 2 | 3.6 | 3.4 | 7.0 |
| 17 | Product of Ex. 4 | 2 | 3.6 | 1.7 | 5.3 |
| 18 | Product of Ex. 5 | 2 | 4.4 | 5.5 | 9.9 |

EXAMPLES 19-23

An alkyd resin paint is prepared in accordance with the following formulation:
 40 parts of Alphthalate ® 380 (60% solution in xylene), alkyd resin may by Reichhold Albert Chemie AG,
 10 parts of iron oxide red 225 made by Bayer AG,
 13.6 parts of talc (micronized),
 13 parts of micronized calcium carbonate (Millicarb ®, Pluss-Stafer AG),
 0.3 part of anti-skinning agent Luaktin ® (BASF),
 0.6 part of cobalt naphthenate (8% metal) and
 22.5 parts of 6:40 xylene/propylene glycol monomethyl ether mixture.

The paint is ground with glass beads to a pigment and filler particle size of 10–15 μm. The corrosion inhibitors indicated in Table III below are added before grinding.

The paint is sprayed onto sand-blasted steel sheets measuring 7×13 cm in a layer thickness amounting to approximately 50 μm after drying. After drying at room temperature for 7 days, the samples are subjected to aftercuring at 60° C. for 60 minutes.

Two cruciform cuts of length 4 cm are cut, down to the metal, in the cured paint surface by means of a bonder cross-cut apparatus. The edge are protected by applying an edge-protection agent (Icosit ® 225) to the latter.

The samples are now subjected to a salt spray test as specified in ASTM B 117 of a duration of 600 hours. After every 200 hours weathering, the state of the coating is assessed, specifically the degree of blistering (as specified in DIN 53,209) at the cross-cut and on the painted surface and also the degree of rusting (as specified in DIN 53,210) on the whole surface.

At the end of the tests, the coating is removed by treatment with concentrated sodium hydroxide solution, and the corrosion of the metal at the cross-cut (as specified in DIN 53,167) and over the remainder of the surface is assessed. In each case the assessment is carried out in accordance with a 6-point scale. The sum of the assessment of the coating and the assessment of the metal surface gives the anti-corrosion protection value CP. The higher this is the more effective is the inhibitor tested.

Results of the salt spray tests are shown in Table III.

TABLE III

| Example | Corrosion inhibiting additive | % Additive | Assessment of coating | Assessment of metal | C.P. |
| --- | --- | --- | --- | --- | --- |
| 19 | Control | — | 2.0 | 0.6 | 2.6 |

TABLE III-continued

| Example | Corrosion inhibiting additive | % Additive | Assessment of coating | Assessment of metal | C.P. |
|---|---|---|---|---|---|
| 20 | Product of Ex. 2 | 2 | 2.2 | 2.0 | 4.2 |
| 21 | Product of Ex. 3 | 2 | 2.2 | 1.7 | 3.9 |
| 22 | Product of Ex. 1 | 2 | 2.6 | 4.4 | 7.0 |

EXAMPLE 24

A self crosslinking acrylic ester/styrene copolymer is prepared in accordance with the following formulation:
147.2 parts Acronal S 760 (50% aq. solution acrylic ester/styrene copolymer)
0.2 part Pigment distribution aid 2.0 parts Butylglycol
2.0 parts White spirit
1.0 part Nopco 8034
38.0 parts Millicarb 2.7 parts Product of Example 1
16.6 parts Bayferrox 130H The paint is applied as described in Examples 7 to 12, and the prepared plates are subjected to the salt spray procedure previously described in Examples 19 to 23 (120 hours).

The results are set out in Table IV.

TABLE IV

| Example | Corrosion inhibiting additive | % Additive | Assessment of coating | Assessment of metal | C.P. |
|---|---|---|---|---|---|
| — | Control | Nil | 4.4 | 3.8 | 8.2 |
| 24 | Product of Ex. 1 | 2 | 4.8 | 3.9 | 10.6 |

EXAMPLES 25-35

The following Examples are prepared from the acids (A) and amines (B) using the procedure described in Example 1.

| Example | A | B | ANALYSIS | Requires | Found |
|---|---|---|---|---|---|
| 25 | 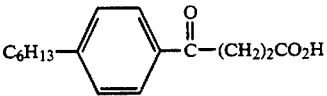 $C_6H_{13}$—⟨phenyl⟩—C(=O)—(CH$_2$)$_2$CO$_2$H | $^tC_{13}H_{27}NH_2$ | C<br>H<br>N | 75.48<br>11.06<br>3.03 | 74.54<br>11.17<br>2.74 |
| 26 | 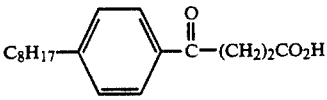 $C_8H_{17}$—⟨phenyl⟩—C(=O)—(CH$_2$)$_2$CO$_2$H | $^tC_{13}H_{27}NH_2$ | C<br>H<br>N | 76.07<br>11.25<br>3.03 | 75.48<br>11.74<br>2.87 |
| 27 | 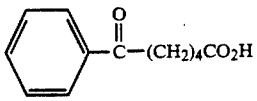 ⟨phenyl⟩—C(=O)—(CH$_2$)$_4$CO$_2$H | $^tC_{13}H_{27}NH_2$ | C<br>H<br>N | 74.07<br>10.62<br>3.46 | 77.65<br>10.74<br>5.35 |
| 28 | 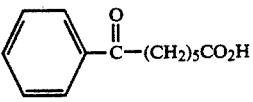 ⟨phenyl⟩—C(=O)—(CH$_2$)$_5$CO$_2$H | $^tC_{13}H_{27}NH_2$ | C<br>H<br>N | 74.46<br>10.74<br>3.34 | 73.85<br>11.01<br>3.89 |
| 29 | 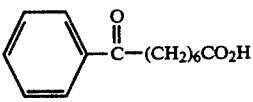 ⟨phenyl⟩—C(=O)—(CH$_2$)$_6$CO$_2$H | $^tC_{13}H_{27}NH_2$ | C<br>H<br>N | 74.82<br>10.85<br>3.23 | 73.93<br>11.09<br>3.24 |
| 30 | 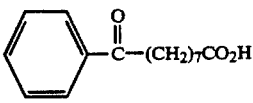 ⟨phenyl⟩—C(=O)—(CH$_2$)$_7$CO$_2$H | $^tC_{13}H_{27}NH_2$ | C<br>H<br>N | 75.17<br>10.96<br>3.13 | 74.60<br>11.22<br>3.27 |
| 31 | 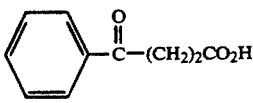 ⟨phenyl⟩—C(=O)—(CH$_2$)$_2$CO$_2$H | $^tC_{13}H_{27}NH_2$ | C<br>H<br>N | 76.45<br>10.80<br>3.88 | 77.23<br>10.36<br>4.16 |
| 32 | 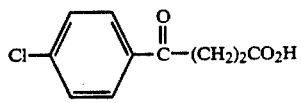 Cl—⟨phenyl⟩—C(=O)—(CH$_2$)$_2$CO$_2$H | $^tC_{13}H_{27}NH_2$ | C<br>H<br>N | 65.93<br>9.07<br>4.57 | 67.07<br>9.23<br>3.40 |

-continued

| Example | A | B | ANALYSIS Requires | Found |
|---|---|---|---|---|
| 33 | Br—⌬—CO—(CH$_2$)$_2$CO$_2$H | $^t$C$_{13}$H$_{27}$NH$_2$ | C 60.52 H 8.39 N 3.06 | 60.04 8.81 3.44 |
| 34 | F—⌬—CO—(CH$_2$)$_2$CO$_2$H | $^t$C$_{13}$H$_{27}$NH$_2$ | C 69.87 H 9.62 N 3.54 | 69.59 10.32 3.71 |
| 35 | H$_3$C—O—⌬—CO—(CH$_2$)$_2$CO$_2$H | $^t$C$_{13}$H$_{27}$NH$_2$ | C 70.76 H 10.07 N 3.44 | 69.18 9.75 4.78 |

EXAMPLES 36–39

An aqueous alkaline paint formulation is prepared as described in Examples 7 to 12. The results of humidity testing are summarised in Table V.

TABLE V

| Example | Corrosion inhibiting additive | % Additive | Assessment of coating | Assessment of metal | C.P. |
|---|---|---|---|---|---|
| 36 | Product of Ex. 27 | 2 | 4.2 | 4.3 | 8.5 |
| 37 | Product of Ex. 28 | 2 | 4.2 | 5.4 | 9.6 |
| 38 | Product of Ex. 30 | 2 | 4.4 | 5.9 | 10.3 |
| 39 | Product of Ex. 32 | 2 | 5.2 | 5.9 | 11.1 |

EXAMPLES 40–48

A similar series of painted plates is also scribed and subjected to a salt spray procedure (168 hours) as previously described. The results of the test are summarised in Table VI.

TABLE VI

| Example | Corrosion inhibiting additive | % Additive | Assessment of coating | Assessment of metal | C.P. |
|---|---|---|---|---|---|
| 40 | Product of Ex. 25 | 2 | 2.8 | 1.3 | 4.1 |
| 41 | Product of Ex. 26 | 2 | 3.4 | 0.6 | 4.0 |
| 42 | Product of Ex. 27 | 2 | 2.4 | 3.5 | 5.9 |
| 43 | Product of Ex. 28 | 2 | 2.7 | 4.1 | 6.8 |
| 44 | Product of Ex. 29 | 2 | 2.9 | 3.4 | 6.3 |
| 45 | Product of Ex. 30 | 2 | 2.4 | 4.7 | 7.1 |
| 46 | Product of Ex. 31 | 2 | 2.4 | 5.5 | 7.9 |
| 47 | Product of Ex. 32 | 2 | 3.4 | 5.7 | 9.1 |
| 48 | Product of Ex. 35 | 2 | 2.0 | 3.7 | 5.7 |

We claim:
1. A coating composition comprising
a) an organic film-forming binder; and
b) a corrosion-inhibiting amount of a water-insoluble salt of
   i) a ketoacid having the formula (I):

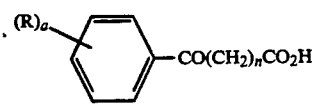

(I)

wherein
a is 1, 2, 3, 4 or 5;
the R substituents are the same or different and each is hydrogen; halogen; nitro; cyano; CF$_3$; C$_1$–C$_{15}$ alkyl; C$_5$–C$_{12}$ cycloalkyl; C$_2$–C$_{15}$ alkenyl; C$_1$–C$_{12}$ halogenoalkyl; C$_1$–C$_{12}$ alkoxy; C$_1$–C$_{12}$ thioalkyl; C$_6$–C$_{12}$ aryl; C$_6$–C$_{10}$ aryloxy; C$_7$–C$_{12}$ arkyl; —CO$_2$R$_1$ is a) hydrogen, b) C$_1$–C$_{20}$ alkyl or said alkyl interrupted by one or more O—, N— or S—atoms, c) C$_7$–C$_{12}$ aralkyl or d) C$_6$–C$_{12}$ aryl or said aryl substituted with one or more carboxy groups; —COR$_1$ in which R$_1$ has its previous significance; NR$_2$R$_3$ in which R$_2$ and R$_3$ are the same or different and each is hydrogen or C$_1$–C$_{24}$ alkyl or said alkyl interrupted by one or more O, S or NH moieties; or when a is 2, 3, 4 or 5, two adjacent groups R may be the atoms required to form a fused benzene or cyclohexyl ring; and
n is an integer from 1 to 10; and
ii) an amine of formula II:

(II)

wherein
X, Y and Z are the same or different, and are hydrogen; C$_8$–C$_{24}$ alkyl or said alkyl interrupted by one or more O-atoms; phenyl; $C_7$–$C_9$ phenylalkyl; $C_7$–$C_9$ alkylphenyl; or two of X, Y and Z together with the N-atom to which they are attached form a 5-, 6- or 7-membered heterocyclic residue, or said residue containing a further oxygen, nitrogen or sulphur atom or said residue substituted by one or more $C_1$–$C_4$ alkyl, amino, hydroxy, carboxy or $C_1$–$C_4$ carboxy alkyl groups, and the other of X, Y and Z is hydrogen; provided that X, Y and Z are not simultaneously hydrogen.

2. A composition according to claim 1 wherein n is 1, 2, 3 or 4.

3. A composition according to claim 2 wherein n is 2 or 3.

4. A composition according to claim 1 wherein R is hydrogen or $C_1$–$C_{15}$ alkyl and a is 1 to 4.

5. A composition according to claim 1 wherein the amine of formula II is a $C_8$–$C_{24}$ primary or secondary amine.

6. A composition according to claim 5 wherein the amine of formula II is a $C_8$–$C_{14}$ primary or secondary amine.

7. A composition according to claim 1 wherein a is 1 to 4, R is hydrogen, $C_1$–$C_{15}$ alkyl, halogen, $C_1$–$C_4$ alkoxy or, if a is at least 2, two adjacent groups R form a fused benzo ring, n is 2 to 7, X is $C_8$–$C_{14}$ alkyl and Y and Z are hydrogen.

8. A composition according to claim 1 wherein the organic film-forming binder component a) is an epoxy resin, a polyurethane resin, an aminoplast resin; an acrylic resin; an acrylic copolymer; a polyvinyl resin; a phenolic resin; a styrene-butadiene copolymer; a polyester resin; an alkyd resin; a mixture of such resins; or an aqueous basic or acid dispersion of such resins; or an aqueous emulsion of such resins.

9. A composition according to claim 8 wherein the epoxy resin is one based on aromatic polyols.

10. A composition according to claim 8 wherein the acrylic polymer is a vinyl acrylic polymer or a styrene acrylic copolymer.

11. A composition according to claim 1 wherein, in addition to components a) and b), one or more of a pigment, dye, extender and other conventional coating composition additive is also present.

12. A composition according to claim 11 wherein a basic extender or pigment is present.

13. A composition according to claim 1 further comprising a further organic, metal-organic or inorganic corrosion inhibitor.

14. A composition according to claim 1 wherein the component b) is present in amount of 0.01–20% by weight, based on the solids content of the coating compositions.

15. An aqueous electrodepositable coating composition according to claim 1 comprising a) an aqueous film-forming binder; and a corrosion inhibiting amount of a water-insoluble salt component b), as defined in claim 1.

16. An aqueous composition according to claim 15 wherein the binder a) is an acrylic polymer, a polybutadiene copolymer or an adduct of an epoxide resin with an amine.

* * * * *

UNITED STATES PATENT AND TRADEMARK OFFICE
CERTIFICATE OF CORRECTION

PATENT NO. : 5,128,396

DATED : July 7, 1992

INVENTOR(S) : ROBERT MONTGOMERY O'NEIL, ET AL.

It is certified that error appears in the above-identified patent and that said Letters Patent is hereby corrected as shown below:

Column 14, line 20, that portion of the line reading "-$CO_2R_1$ is a)" should read --$CO_2R_1$ in which $R_1$ is a) --.

Signed and Sealed this

Twenty-sixth Day of October, 1993

*Attest:*

BRUCE LEHMAN

*Attesting Officer*  *Commissioner of Patents and Trademarks*